United States Patent [19]
Chien

[11] Patent Number: 5,035,146
[45] Date of Patent: Jul. 30, 1991

[54] METHOD AND APPARATUS FOR DETERMINING STEAM QUALITY AND/OR FLOW RATE FROM IMPACT FORCE AND FLOW RESTRICTION DATA

[75] Inventor: Sze-Foo Chien, Houston, Tex.

[73] Assignee: Texaco Inc., White Plains, N.Y.

[21] Appl. No.: 545,223

[22] Filed: Jun. 28, 1990

[51] Int. Cl.$^5$ .............................................. G01F 1/74
[52] U.S. Cl. ................... 73/861.04; 73/29.01; 73/195
[58] Field of Search ................. 73/29.01, 29.03, 29.05, 73/861.04, 195

[56] References Cited

U.S. PATENT DOCUMENTS

| | | | |
|---|---|---|---|
| 2,439,723 | 8/1948 | Engdahl | 73/861.04 |
| 3,408,866 | 11/1968 | Gibson et al. | 73/861.04 |
| 4,836,032 | 6/1989 | Redus et al. | 73/861.04 |

FOREIGN PATENT DOCUMENTS

0166417 12/1981 Japan ................................. 73/861.04

Primary Examiner—Herbert Goldstein
Attorney, Agent, or Firm—Jack H. Park; Kenneth R. Priem

[57] ABSTRACT

A method and apparatus for determining the quality of steam and steam flow rate use the thrust or impact force of the steam against a device in the steam flow path and restriction data from a choke or orifice plate. The impact force can be read from a variety of devices mounted in the steam flow path and using known electrical and/or mechanical reading and recording techniques. The restriction data can be derived from measurements taken across known flow restriction devices such as an orifice plate or a choke.

14 Claims, 3 Drawing Sheets

METHOD AND APPARATUS FOR DETERMINING STEAM QUALITY AND/OR FLOW RATE FROM IMPACT FORCE AND FLOW RESTRICTION DATA

BACKGROUND OF THE INVENTION

1. The Field of the Invention

The present invention pertains to a method and apparatus for determining the quality and/or flow rate of steam from impact force and flow restriction data.

2. The Prior Art

Steam flooding has become an accepted practice for secondary recovery of petroleum products from marginal fields or heavy oil reservoirs that require a degree of stimulation to produce a satisfactory flow of crude petroleum. There is a need for a simple method and apparatus to determine the quality of steam at the wellhead of a well injecting steam into the formation to be stimulated. Such a measurement, if simplified, would be particularly useful in determining the amount of heat which is applied to the underground reservoir by the injected steam.

The measurement or monitoring of steam quality is important since the steam's quality, and thereby its reservoir or formation heatup effect, directly affects the resulting production operations. Further, the quality of the steam which can be most economically injected into a particular substrate or reservoir is contingent on a number of circumstances. The latter include the depth of the reservoir and the anticipated prospects for extracting commercially justified amounts of hydrocarbon products therefrom.

In brief, it is desirable that the quality of steam which is injected at each injection well be altered or adjusted to a level of quality that best conforms to the condition of the formation penetrated by that well. Clearly the quality of the steam must be known before any alteration or adjustment can be made.

It is known that in order to be particularly effective in this type of stimulation operation, the flow of injected steam must be monitored by use of metering means positioned in the steam-carrying line adjacent the wellhead. It can be appreciated that steam will normally leave the steam generator or source at a known quality, pressure and mass flow rate. As the pressurized steam flow progresses towards an injection well, however, the quality will usually be substantially decreased. A decrease in the quality can be based on such factors as the distance between the well and the source, the effectiveness of pipe insulation and weather conditions including both ambient temperature and wind velocity. It will further depend on the pipe layout, including the number and orientation of fittings through which the steam has to travel prior to reaching the injection port or well, because of phase separation that can occur in these fittings.

It is important, therefore, as a matter of economic practicality, that a flow monitoring and controlling means be instituted into the steam-carrying conduit immediately upstream of each injection wellhead. A choke mechanism or an orifice plate in the steam line will function to constrict the steam flow to thereby allow regulation of the steam mass flow rate which enters that particular well.

U.S. Pat. No. 4,836,032, discloses the use of an orifice plate in series with a critical flow choke to provide a method of measurement for both steam quality and mass flow rate. Either the orifice plate or the choke alone can be used to measure steam quality and mass flow rate. However, a mathematical expression for steam quality through both devices is obtained by solving an independent mass flow rate equation for each device, an equation for wet steam through the critical flow choke and an equation for wet steam through a sharp-edged orifice plate.

BRIEF SUMMARY OF THE INVENTION

The present invention concerns a method and apparatus for measuring steam quality (mass of steam vapor divided by the total mass of water and steam vapor) of wet steam having an unknown water content. The invention comprises, in brief, a method and apparatus to determine the quality of product stimulation wet steam which is to be injected into a well for producing hydrocarbon products from a reservoir being steamflooded for secondary oil recovery. The method is based on the determination of certain characteristics of steam at the injection wellhead. Knowing these characteristics will permit the desired quality determination to be made and, therefore, making appropriate adjustments of the steam quality for efficient oil recovery. More precisely, the method and apparatus of the present invention are addressed to measuring steam quality and adjusting flow rate in a steam line to a desired degree prior to injection of the steam flow into a hydrocarbon-containing substrate by means of an injection well.

Stated in another way, in any process involving steam injection for a secondary oil recovery procedure, a persistent problem exists in making a rapid and accurate determination of the quality and mass flow rate of steam being injected into an individual well or a group of wells. Such knowledge is relevant to production efficiency because the steam quality and mass flow rate directly affect the production operation at the production well and, consequently, the investment requirements for similar steam flooding projects.

It is known to be desirable, and highly practical from an economic consideration, to mix water with high quality steam for achieving a lower, but adequate, quality steam at each specific wellhead. In such an instance the present invention provides for a means and method to quickly and accurately determine the quality of the steam and its mass flow rate.

It has been determined, for instance, that as much as 20,000 barrels of oil a day must be burned to generate sufficient high-quality wet steam for the production of hydrocarbons in a typical enhanced oil recovery operation in a field. The cost efficiency of this type of steam flood operation can be improved noticeably by economizing the distribution of the steam.

Steam quality tapering, and conversion to hot water floods at various field well patterns, have mandated the accurate measurement of steam quality and mass flow rates at individual injection wells. Also, the phenomena of two-phase flow in pipes, as well as phase splitting, have caused steam qualities and mass rates at injection heads to be greater or less than the desired qualities necessary for effective reservoir management.

It is therefore an object of the present invention to provide a method and apparatus for determining the quality of the steam which is injected into a reservoir as the stimulating media in a steam flooding or steam simulation operation.

It is a further object to provide a method and apparatus for readily determining the quality and mass flow rate of wet steam being injected into a hydrocarbon producing reservoir whereby the hydrocarbon production efficiency is improved.

It is still further object to provide means for measuring the quality and adjusting the flow rate of steam, under critical flow, which is injected into a hydrocarbon-producing substrate by measurement of the impact force of the steam.

The present invention is distinguished from the prior art methods by use of impact force data and flow restriction data to determine steam quality and steam flow. The impact force experienced by means in the steam flow is primarily a function of the mass flow rate and flow velocity.

BRIEF DESCRIPTION OF THE DRAWINGS

The present invention will now be described, by way of example, with reference to the accompanying drawings in which.

DETAILED DESCRIPTION OF THE PREFERRED EMBODIMENT

Figure 1:
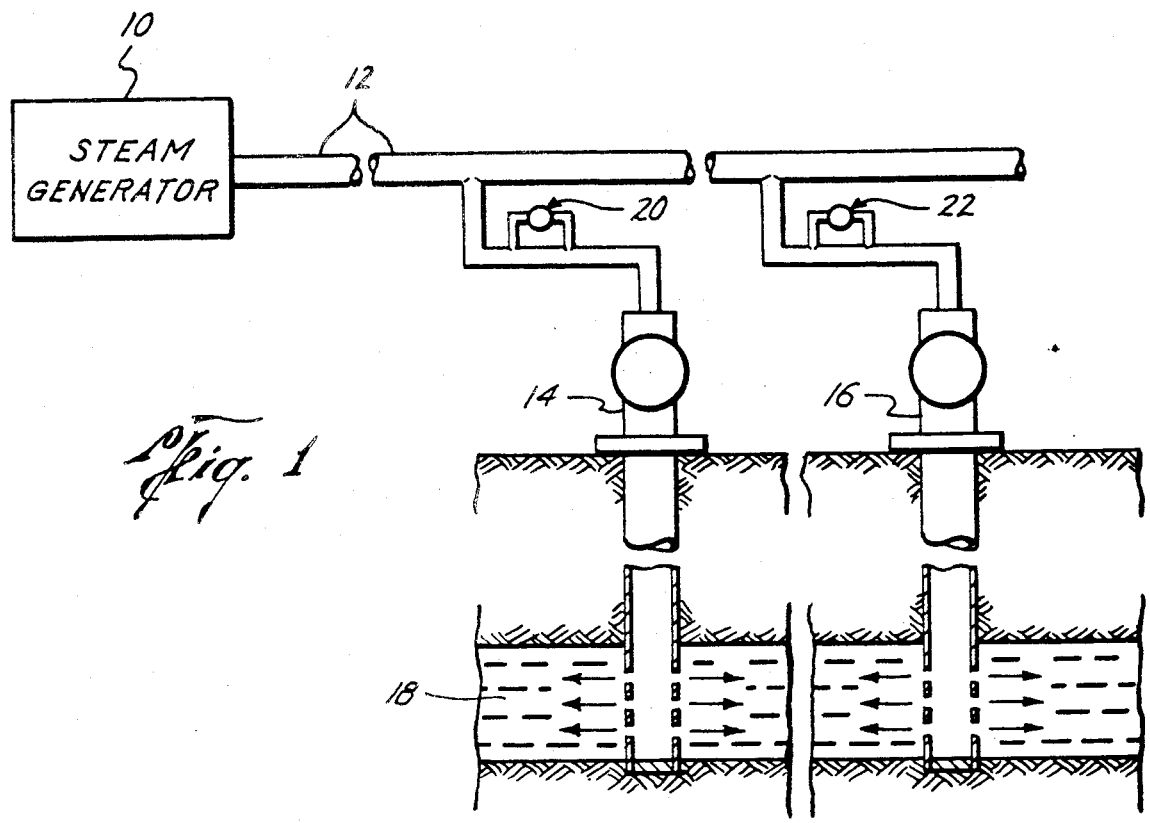
FIG. 1 is a schematic representation of the present invention incorporated into a steam pipe distribution system for a typical steam flood, enhanced oil recovery operation.

The present invention, with reference to FIG. 1, relates to a method and apparatus for determining the quality and mass flow rate of a steam flow. This determination is usually made immediately prior to the steam being injected into a hydrocarbon containing reservoir. The steam is generated by generator 10 and fed by a series of pipes 12 to individual injection wellheads 14, 16 for injection into a substrate 18. Immediately upstream of the respective wellheads are steam quality measurement devices 20, 22 in accordance with the present invention. It is readily appreciated that the steam coming from the generator 10 will deteriorate in quality as it passes through the pipes 12, particularly when the steam encounters a splitter or other obstruction (not shown) to a straight line flow. As the steam travels through the pipes 12, there is the general tendency to form an annular flow with the liquid phase being adjacent to the walls of the pipe and the gaseous phase following generally axially along the pipe. This flow pattern will be disrupted by almost every encounter with a joint or fitting of the pipe. The mixture of the liquid and vapor phases thus is largely determined by the distance traveled between generator 10 and wellhead 14, 16, the insulation on the pipe, the path or route taken by this steam insofar as splitting, bending or other deviations from an axial course and even the weather including ambient temperature and wind velocity.

Referring to FIG. 1, the normally insulated steam flow pipeline or conduit 12 includes fittings, couplings, flanges and the like (all of which are known and none of which have been shown for sake of simplicity of the drawings) into which a flow of steam is directed from a pressurized source, namely the generator 10, to the wellheads 14, 16. Steam from the source 10 preferably is of a quality between 10 and 80 percent and has a mass flow rate from 100 to 400 barrels of steam per day cold water equivalent (BSPD-CWE) and a pressure between 300 and 700 psig. It is submitted that the present invention will work over flow rate ranges from 50 to 5000 BSPD-CWE and pressures from 100 to 3000 psig with appropriate modification of the empirical constants. Operationally, the steam issuing from the high pressure source will be of a known quality, depending primarily upon its water content.

Figure 2:
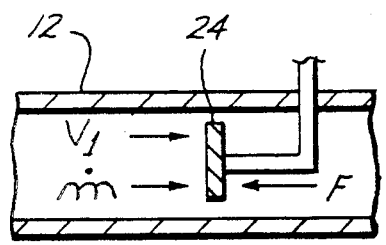
FIG. 2 is a schematic section illustrating the principles of the present invention.

The impact force experienced by an obstacle, such as the force measurement plate 24 shown in FIG. 2, in the flowing stream is primarily a function of the mass flow rate and flow velocity of the steam. The plate 24 or similar force measurement means (not shown) is mounted in the conduit 12 by known mean to be responsive to the impact force of the steam to give force measurement readings by known electrical or mechanical means (not shown). The plate 24 or similar means, are used in combinations with an orifice plate 26 or choke 28 to form the measurement devices 20, 22. The orifice plate has an axial orifice 30 and is spanned by a differential pressure meter 32. The choke 28 has a profile axial bore 34 and likewise is spanned by a differential pressure meter 36.

The impact force measured by the plate 24 or similar means will be:

$$F \propto \dot{m} V_1$$

where
$\dot{m}$ = mass flow rate
$V_1$ = Velocity of fluid flow
or $$F = K \dot{m} V_1 \quad (1)$$

where K is a constant depending on fluid properties, geometry etc., and must be determined by experimentation.

Figure 3A:
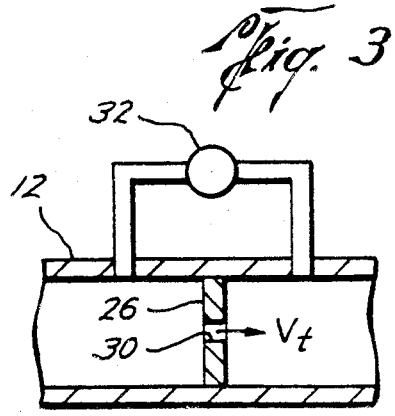
FIGS. 3a and 3b are schematic sections of an orifice plate and a nozzle, respectively, serving as flow restriction devices.
Figure 3B:
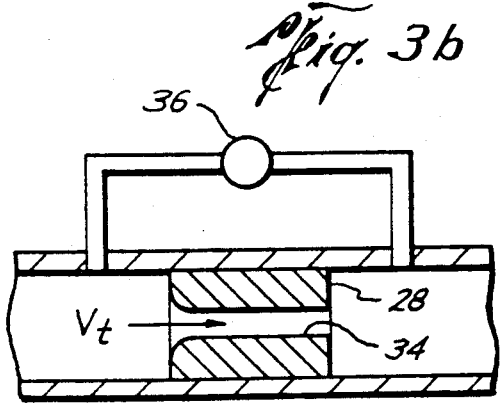

The flow restriction could be in the form of either an orifice plate 26 or choke 28 as shown in FIG. 3a or 3b, wherein $V_t$ is the throat velocity, or velocity of flow through the flow restriction orifice 30 or passage 34, respectively.

Both the mass flow rate, m, and the velocity, $V_t$, can be expressed in terms of pressure drop across the flow restriction and the density of the fluid:

$$m \propto (\Delta P, \rho) \text{ or } m = B \sqrt{\Delta P \rho} \quad (2)$$

$$V_t \propto (\Delta P, \rho) \text{ or } V_t = C \sqrt{\Delta P / \rho} \quad (3)$$

where B and C are conversion constants depending on the diameter of the restriction. Furthermore, the exact form of the equations (1), (2) and (3) may have to be determined experimentally and assuming the ratio between the average and throat velocity is a constant, $$\frac{V_1}{V_t} = \Phi, \quad (4)$$

By combining equations (1), (2), (3) and (4), Eq. (1) becomes a function of density.

$$F = F(\rho) \quad (5)$$

Since the magnitude of F is measured, the value of $\rho$ can be solved from Equation (5).

Once the density of the fluid is known, the quality can be determined.

$$\frac{1}{\rho} = Xv_g + (1-x)v_g \quad (6)$$

where X is quality and $v_f$ and $v_g$ can be determined from steam tables knowing steam pressure and temperature. The flow rate can be solved from Equation (2).

The apparatus for carrying out the subject method can be in a number of forms, as shown by the examples in FIGS. 4a to 4f which should not be considered as limitations to the scope of this invention.

Figure 4A:
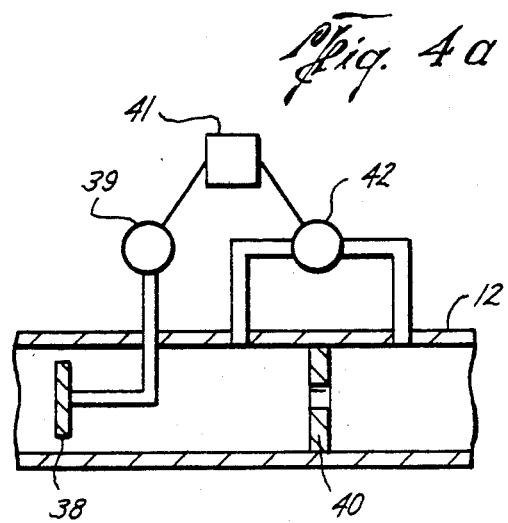
FIGS. 4a to 4f schematic sections showing alternate embodiments of the present invention.
Figure 4B:
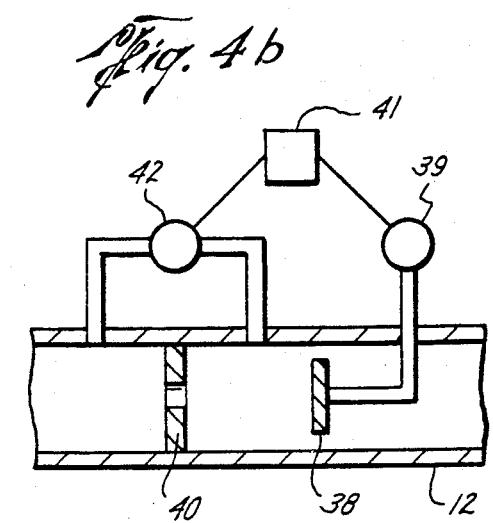
Figure 4C:
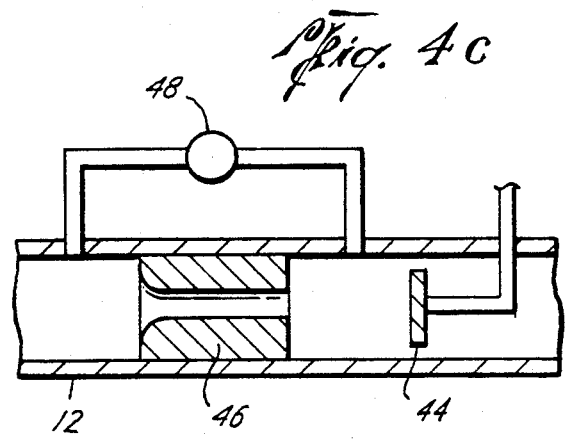
Figure 4D:
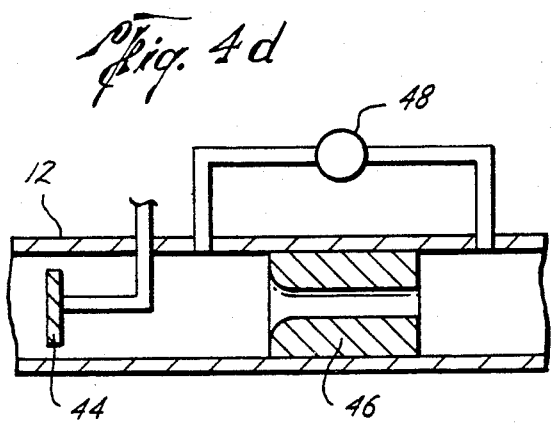
Figure 4E:
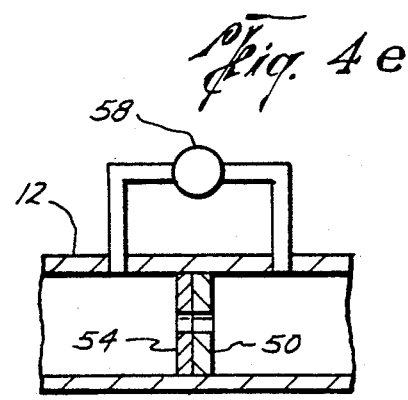
Figure 4F:
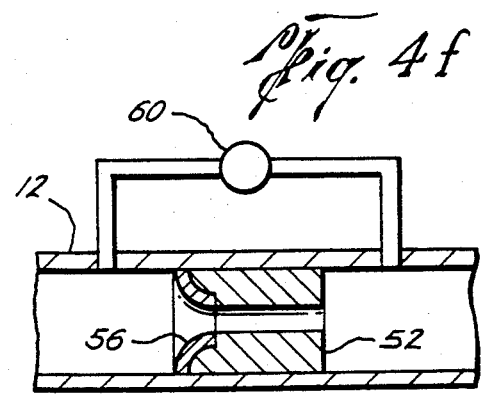

FIGS. 4a and 4b show reverse arrangements of a force measurement plate 38 upstream of and downstream from an orifice plate 40. In each case the plate is connected to electrical and/or mechanical measuring and recording means 39 and differential pressure measuring means 42 spans the orifice plate 40. Means 41 receives impact force and pressure drop input from recording means 39 and differential pressure measuring means 42, respectively, and calculates the steam quality and flow rate. FIGS. 4c and 4d show similar arrangements for a force measurement plate 44 and a choke 46 and differential pressure measuring means 48. FIGS. 4e and 4f are somewhat different from the preceding embodiments in that there is no separate force measurement means. Instead the orifice plate 50 and choke 52 have on their upstream faces pressure sensitive means 54, 56, respectively, which pressure sensitive means can be selected from a wide variety of known devices and materials. Piezoelectric crystals are just one example of suitable pressure sensing means. These embodiments also include differential pressure measuring means 58, 60, respectively. The measuring and recording means and calculating means have not been shown with the embodiments of FIGS. 4c to 4f.

An Orifice Flow Equation, such as that proposed by Murdock or James, (see "Two Phase Flow Measurement With Orifices" by J. W. Murdock Journal of Basic Engineering Transcript ASME Series D Vol 84 1962 pp 419–432 and "Metering of Steam-Water Two Phase Flow by Sharp-Edged Orifices" by R. James Proceedings of Inst. Mechanical Engineers Vol. 180. Pt 1, N. 23 1965-66 pp 549–566) and Choke Equation, such as that proposed by Napier (see "A Study of Slip Ratios for the Flow of Steam-Water Mixtures at High Void Fractions" by W. H. Vance PhD Thesis University of Washington 1962) can be used to determine steam quality if the mass flow rate of the flow is given. Conversely, such equation can be used to determine the mass flow rate if the steam quality is a known value. Obviously, the orifice pressure or choke flow information alone is not sufficient to determine both the flow rate and quality. Another set of information, independent of the orifice, is required to solve both the flow rate and steam quality. According to the present invention, Thrust or Impact Force measurement can be used in conjunction with the orifice information to obtain both the flow rate and steam quality. Since the orifice flow equation and choke flow equation have been relatively well established, only obtaining the thrust equation will be presented in the following discussion. This equation shows that the thrust or impact force information is definitely related to the flow rate and quality. Validity of the equation is further proved by using published experimental data.

Derivation of the Thrust or Import Force Equation is through following steps:
1. Thrust (or Impact Force) as a momentum of the flow,
2. Velocities in terms of two-phase flow parameters,
3. Thrust of two-phase flow,
4. The Thrust Equation simplified by using a slip velocity ratio-quality relationship developed by the present inventor,
5. The thrust equation as tested by the published data of Vance (cited above) who was interested in the slip ratios of wet steam at high void fractions.

Wet steam flowing out of a first pipe or conduit and impinging on the opposite wall of a transverse second pipe or conduit causes the velocity of the steam to change sharply as it hits the transverse wall, which is perpendicular to the flow direction of the steam. Assume the static pressure at the exit of the first pipe or conduit is the same as that at the wall and the area of the impact is approximately the same as the pipe or conduit area. The momentum balance gives:

$$F = \frac{1}{g_c}(m_g v_g + m_f v_f) \quad (7)$$

where
F is the Thrust Force experienced on the transverse wall
$m_g$ is the mass flow rate of the vapor phase of the steam,
$m_f$ is the mass flow rate of the liquid phase of the steam,
$V_g$ is the average velocity of the vapor phase of the steam,
$V_f$ is the average velocity of the liquid phase of the steam,
The mass flow rate m is the sum of the vapor and liquid phase $$m = m_g + m_f = GA \quad (8)$$

$$X + \frac{m_g}{m} + \frac{m_g}{m_g + m_f} \quad (9)$$

where
G is the mass flux and
X = steam quality.
Introducing Eq. (8) and Eq. (9) into Equation (7), one obtains $$F = \frac{GA}{g_c}[XV_g + (1-x)V_f] \quad (10)$$

The tube area, in terms of two phase flow, is composed of the area occupied by the vapor phase, $A_g$ and the area occupied by the liquid phase, $A_f$.

$$A = A_g + A_f \quad (11)$$

The Void Fraction of each phase is:

$$R_g = \frac{A_g}{A} = \text{Void Faction of Vapor Phase} \quad (12)$$

-continued $$R_f = \frac{A_f}{A} = (1 - R_G) = \text{Void Fraction of Liq. Phase} \quad (13)$$

$$R_g + R_f = 1 \quad (14)$$

Continuity Equation of each phase:

$$m_g = \frac{A_g V_g}{v_g} \text{ or } V_g = \frac{m_g v_g}{A_g} \quad (15)$$

$$m_f = \frac{A_f V_f}{v_f} \text{ or } V_f = \frac{m_f v_f}{A_f} \quad (16)$$

$v_f$ and $v_g$ are the specific volume of liquid phase and vapor phase, respectively.

From Eq. (9):

$$\dot{m}_g = X\dot{m} = XGA$$

$$\dot{m}_f = (1-x)\dot{m} = (1-x)GA$$

and from Eq. (12) and (13):

$$A_g = A R_g$$

$$A_f = A R_f$$

These equations reduce Eq. (15) and (16) to:

$$V_g = \frac{\dot{m} v_g}{A_g} = \frac{\dot{m} X v_g}{A R_g} = \frac{G X v_g}{R_g} \quad (17)$$

$$V_f = \frac{\dot{m}_f v_f}{A_f} = \frac{(1-x)G A v_f}{A R_f} = \frac{(1-x)G v_f}{R_f} \quad (18)$$

Introducing the slip Velocity Ratio K:

$$K = \frac{V_g}{V_f} = \frac{G X v_g}{R_g} \cdot \frac{R_f}{G(1-x)v_f} \quad (19)$$

$$= \frac{X}{1-x} \cdot \frac{R_f}{R_g} \cdot \frac{v_g}{v_f}$$

which, by using $R_f + R_g = 1$, may reduce to either:

$$R_f = \frac{K(1-x)v_f}{Xv_g + K(1-x)v_f} \quad (20)$$

or $$R_g = \frac{Xv_g}{Xv_g + K(1-X)v_f} \quad (21)$$

combining Eq. (17) with Eq. (21):

$$V_g = G[Xv_g + K(1-x)v_f] \quad (22)$$

And, combining Eq. (18) with Eq. (20):

$$V_f = \frac{G}{K}[Xv_g + K(1-x)v_f] \quad (23)$$

Introducing Eq. (22) and Eq. (23) to Eq. (10):

$$F = \frac{GA}{g_c} \left\{ XG[Xv_g + K(1-x)v_f] + \quad (24) \right.$$

-continued $$\left. (1-x)\frac{G}{K}[Xv_g + K(1-x)v_f] \right\}$$

or $$\frac{Fg_c}{G^2 A v_f} = \left[ x^2 + \frac{x-x^2}{K} \right] \frac{v_g}{v_f} + (x - x^2)K + (1-x)^2 \quad (25)$$

Eq. (24) is the basic Thrust (Impact Force) Equation for Two-phase Flow, while Eq. (25) expresses the equation in dimensionless form. Eq. (24) gives the absolute magnitude of the thrust force experienced by the plate, while Eq. (25) is useful to correlate experimental data. Either one of these equations may be used with an appropriate orifice flow equation to simultaneously solve the flow rate and the steam quality.

In steam flood applications, one is more interested in the steam quality in the 10 to 80% range. Based on Vance's experimental data, an empirical correlation between Slip Ratio and Steam Quality is established for this quality range.

$$K = X^{-0.398} \quad (26)$$

With this correlation, Eq. (25) can be written:

$$\frac{Fg_c}{G^2 A v_f} + [x^2 + x^{1.398} - x^{2.398}] \frac{v_g}{v_f} + \quad (27)$$

$$(1-x)^2 + (x^{0.602} - x^{1.602})$$

Figure 5:
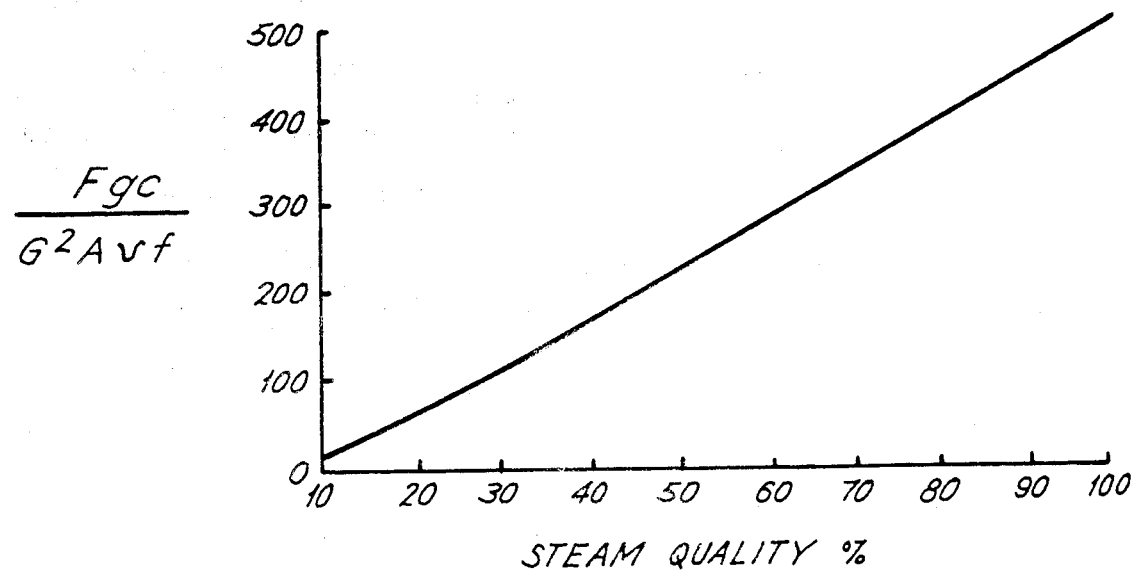
FIGS. 5 and 6 are graphs showing examples of the thrust-quality relationship.

The relation between the dimensionless force $$\frac{Fg_c}{G^2 A v_f}$$

and steam quality X is shown in FIG. 5 as a solid line.

It has been mentioned that the basic Thrust or Impact Force Equation is Equation (25). However, to use it, one must determine or have a slip velocity ratio for the specific condition. The correlation shown in Eq. (27) is an example. However, an improved correlation can be developed and applied if more information on slip ratio and quality relationships is available. The Thrust Equation thus can be used to determine steam quality if the mass flux is known. The mass flux can be determined by an orifice or choke. The following shows mass flux determined by critical flow choke.

As shown in Eq. (25), the Thrust-Flow Rate-Quality Relationship is:

$$\frac{Fg_c}{G^2 A v_f} = \left[ x^2 + \frac{x-x^2}{K} \right] \frac{v_g}{v_f} + (x-x^2)K + (1-x)^2 \quad (28)$$

If the mass flux G is determined by a critical flow choke, the mass flux will be a function of upstream pressure and steam quality. Using a critical flow equation such as Napier's $$G = 2.057 \frac{p}{\sqrt{x}} \quad (29)$$

where p is steam pressure upstream of the choke in psia; x is steam quality expressed in a fraction.

Combining (29) and (30)

$$\frac{Fg_c}{4.231p^2Av_f} = \left(x + \frac{1-x}{K}\right)\frac{v_g}{v_f} + (1-x)K + \frac{(1-x)^2}{x} \quad (30)$$

Knowing steam pressure p, the $v_f$ and $v_g$ can be determined from steam tables. The thrust force becomes a function of K and X. Once quality is determined from Eq. (30), the mass flow rate can be determined from Eq. (29). For example, using the slip ratio between liquid and vapor derived from the Vance data shows:

$$K = X^{-0.398} \quad (31)$$

and Eq. (30) becomes:

$$\frac{Fg_c}{4.231p^2Av_f} = [x + (1-x)x^{0.398}]\frac{v_g}{v_f} + \quad (32)$$

$$(1-x)x^{-0.398} - \frac{(1-x)^2}{x}$$

Equation (32) shows the relationship between F and X can be established once the value of A, p, $v_g$ and $v_f$ are determined.

Example

Steam at 600 psia flowing through a critical flow choke and the force of the discharge is sensed by a force measurement device to determine the relationship between the Impact Force and Steam Quality.

p = 600 psia
$v_f = 0.0201$ ft$^3$/1 bm
$v_g = 0.7689$ ft$^3$/1 bm
According to Eq. (30)

$$\frac{Fg_c}{4.231A0.0201(600)^2} = \left(x + \frac{1-x}{K}\right)\frac{0.7689}{0.0201} +$$

$$(1-x)K + \frac{(1-x)^2}{X}$$

$$\frac{Fg_c}{30615.5A} = 38.253\left(x + \frac{1-x}{K}\right) + \frac{1-x}{K} + \frac{(1-x)^2}{x}$$

For $K = X^{-0.398}$ the values of $$\frac{Fg_c}{30615.51A}$$

are shown in the following table:

| Steam Quality X | $\frac{Fg_c}{30615.5A}$ $K = X^{-0.398}$ |
|---|---|
| 0.01 | 110.64 |
| 0.05 | 34.12 |
| 0.10 | 27.95 |
| 0.20 | 28.50 |
| 0.40 | 33.00 |
| 0.60 | 36.20 |
| 0.80 | 37.87 |
| 1.00 | 38.25 |

Figure 6:
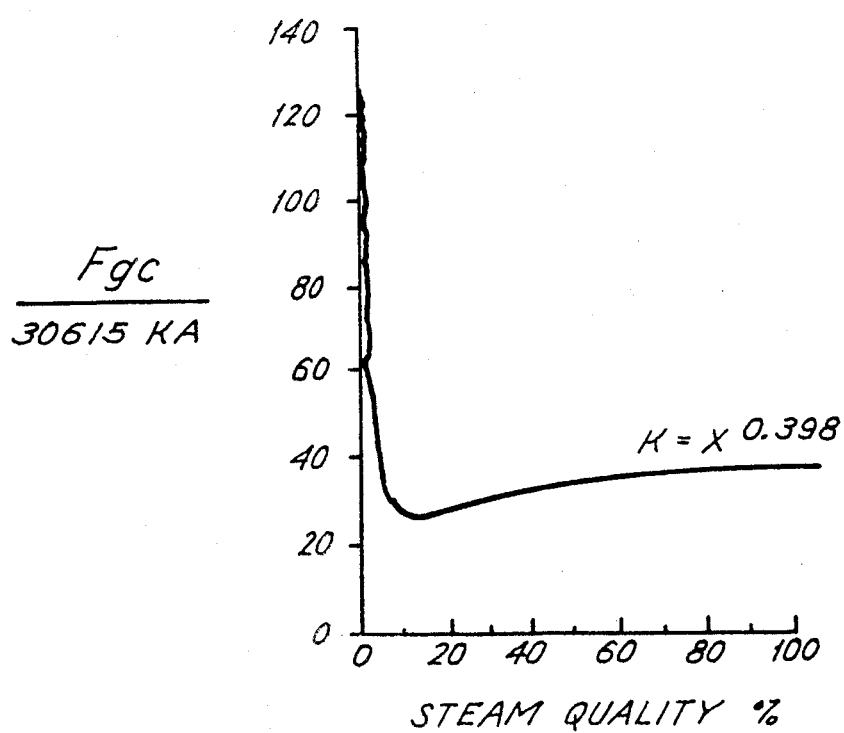

The values of $$\frac{Fg_c}{30615.5A}$$

are plotted against steam quality in FIG. 6.

FIG. 6 shows the thrust force is very sensitive to quality change at very low steam qualities (X less than 20%). Above 20% quality, the thrust force becomes less sensitive to the change in steam quality. It should be emphasized that the thrust force will depend on the slip ratio of the flow. One needs either to assign a value for the slip ratio of the flow or to have a device to determine the slip ratio so that the thrust force can be used to indicate the steam quality in the range of steam quality currently practiced in steam flood projects.

The present invention may be subject to many changes and modifications without departing from the spirit of essential characteristics thereof. The present embodiments are therefor to be in all respects illustrative rather than restrictive of the scope of the invention which is to be determined by the appended claims.

I claim:

1. A method for determining the quality and flow rate of steam, namely a mixture of liquid and vapor flowing through a pipe under subcritical to critical flow conditions comprising the steps of:
    measuring the impact force of the steam flow;
    measuring the pressure differential of the steam flowing through known flow restriction means; and
    calculating the steam quality and flow rate from these measurements.

2. A method according to claim 1 wherein the impact force is determined by $$F = K\dot{m}V_t$$

where
    K is a constant,
    $\dot{m}$ is mass flow rate, and
    $V_t$ is velocity of fluid flow.

3. A method according to claim 1 wherein the mass flow rate and velocity are determined by the pressure drop across the flow restriction and the fluid density:

$$m \propto (\Delta P, \rho) \text{ or } m = B\sqrt{\Delta P/\rho}$$

$$V_t \propto (\Delta, P\rho) \text{ or } V_t = C\sqrt{\Delta P/\rho}$$

4. An apparatus for determining the quality of steam, namely a mixture of liquid and vapor, flowing through a pipe under subcritical to critical flow conditions comprising:
    force responsive means positioned within said pipe and against which said steam impinges to measure the force of the flowing steam;
    means forming a flow restriction in said pipe; and
    means determining the pressure drop across said flow restriction and;
    means to calculate the steam quality and flow rate from said impact force and pressure drop.

5. The apparatus according to claim 4 wherein said force responsive means positioned within the pipe comprises;
    plate means mounted substantially transverse to the steam flow; and means connected to said plate means to measure the thrust forces applied against the plate by the flowing steam.

6. The apparatus according to claim 5 wherein said means to measure the thrust are mechanical.

7. The apparatus according to claim 5 wherein said means to measure the thrust are electrical.

8. The apparatus according to claim 5 wherein said means to measure the thrust are electro-mechanical.

9. The apparatus according to claim 4 wherein said means for determining pressure drop across said restriction comprises:
   an orifice plate fixedly mounted extending transversely across said pipe; and
   means for measuring the difference in pressure on opposite sides of said plate.

10. The Apparatus according to claim 9 wherein said orifice plate is upstream from said force responsive means.

11. The apparatus according to claim 9 wherein said orifice plate is downstream from said force responsive means.

12. The apparatus according to claim 4 wherein said means for determining pressure drop across said restriction comprises:
   choke means fixedly mounted in said pipe; and
   means for measuring the difference in pressure on opposite sides of said choke.

13. The apparatus according to claim 12 wherein said choke means is upstream from said force responsive means.

14. The apparatus according to claim 12 wherein said choke means is downstream of said force responsive means.

* * * * *

UNITED STATES PATENT AND TRADEMARK OFFICE
CERTIFICATE OF CORRECTION

PATENT NO. : 5,035,146

DATED : July 30, 1991

INVENTOR(S) : Sze-Foo Chien

It is certified that error appears in the above-identified patent and that said Letters Patent is hereby corrected as shown below:

Column 4, Line 53 in the equation change "m" (each occurrence) to --$\dot{m}$--

Column 6, Lines 26, 42 and 46 in the equation change "m" (each occurrence) to --$\dot{m}$--

Column 7, Lines 11, 14, 32 and 34 in the equation change "m" (each occurrence) to --$\dot{m}$--

Col. 10, Claim 3, Line 4, in the equation change "m" (each occurrence) to --$\dot{m}$--

Signed and Sealed this

Twenty-second Day of December, 1992

Attest:

DOUGLAS B. COMER

*Attesting Officer*   *Acting Commissioner of Patents and Trademarks*